United States Patent
Campbell et al.

(10) Patent No.: US 6,524,278 B1
(45) Date of Patent: Feb. 25, 2003

(54) NEEDLE SHEATH

(75) Inventors: John Campbell, Zionsville, IN (US); John Targell, Ayrshire (GB)

(73) Assignee: NMT Group PLC (GB)

(*) Notice: Subject to any disclaimer, the term of this patent is extended or adjusted under 35 U.S.C. 154(b) by 0 days.

(21) Appl. No.: 09/563,268

(22) Filed: May 3, 2000

Related U.S. Application Data

(63) Continuation of application No. PCT/GB99/01175, filed on Jul. 7, 1999.

(30) Foreign Application Priority Data

| Sep. 4, 1998 | (GB) | ............................................. 9819217 |
| Mar. 31, 1999 | (GB) | ............................................. 9907274 |
| Mar. 3, 2000 | (GB) | ............................................. 0005086 |

(51) Int. Cl.[7] .............................................. A61M 5/32
(52) U.S. Cl. .................. 604/192; 604/164.08; 604/162; 604/263; 604/110
(58) Field of Search ..................... 600/577; 604/164.08, 604/162, 192, 263, 110, 167.02, 167.03

(56) References Cited

U.S. PATENT DOCUMENTS

| 2,460,039 A | 1/1949 | Scherer et al. |
| 3,306,290 A | 2/1967 | Weltman |
| 3,314,428 A | 4/1967 | Johnson et al. |
| 3,736,932 A | 6/1973 | Satchell ................... 128/218 R |
| 3,886,930 A * | 6/1975 | Ryan .......................... 600/577 |
| 3,941,129 A | 3/1976 | Pleznac |
| 4,009,716 A | 3/1977 | Cohen |
| 4,066,079 A | 1/1978 | Chiarolla ................ 128/218 N |
| 4,214,584 A | 7/1980 | Smirnov et al. |
| 4,316,463 A | 2/1982 | Schmitz et al. |
| 4,333,456 A | 6/1982 | Webb |
| 4,333,458 A | 6/1982 | Margulies et al. |

(List continued on next page.)

FOREIGN PATENT DOCUMENTS

| CL | 37603 | 9/1983 | |
| EP | 0 201 611 A1 | 11/1986 | ............ A61M/5/32 |
| EP | 0210160A1 B1 B2 | 1/1987 | |
| EP | 0413414A1 B1 | 8/1989 | |

(List continued on next page.)

OTHER PUBLICATIONS

English translations of the abstracts for TW 167913, TW142558, TW225161, TW216518, and TW154735.
First page with abstract of WO 90/06146 which is the English language equivalent to HU206457.
Copy of English translation of the Abstract of Chilean Patent No. CL37603.
Copy of European Search Report dated Sep. 14, 2000.
Copy of English translation of the claims of NL8900208.

*Primary Examiner*—Teresa Walberg
*Assistant Examiner*—Fadi H. Dahbour
(74) *Attorney, Agent, or Firm*—Baker & Daniels

(57) ABSTRACT

A sheath for sheathing the needle of a hypodermic syringe and penetrating the rubber cap of a vial or the like, the sheath having apertures therein to allow the ingress of liquid into a zone thereof with which the needle communicates so that the liquid drawn through the needle during filling of the syringe first enters that zone before entering the needle. The sheath is further provided with a filter element and/or a needle-wiping element.

38 Claims, 5 Drawing Sheets

U.S. PATENT DOCUMENTS

| | | | |
|---|---|---|---|
| 4,507,117 A | 3/1985 | Vining et al. | |
| 4,650,468 A | 3/1987 | Jennings, Jr. | |
| 4,675,005 A | 6/1987 | DeLuccia | |
| 4,687,467 A | 8/1987 | Cygielski | |
| 4,692,156 A | 9/1987 | Haller | |
| 4,695,274 A | 9/1987 | Fox | |
| 4,702,738 A | 10/1987 | Spencer | |
| 4,710,170 A | 12/1987 | Haber et al. | |
| 4,737,150 A | 4/1988 | Baeumle et al. | 604/198 |
| 4,747,831 A | 5/1988 | Kulli | |
| 4,767,413 A | 8/1988 | Haber et al. | |
| 4,770,655 A | 9/1988 | Haber et al. | |
| 4,775,369 A * | 10/1988 | Schwartz | 604/263 |
| 4,790,822 A | 12/1988 | Haining | |
| 4,801,295 A | 1/1989 | Spencer | |
| 4,804,370 A | 2/1989 | Haber et al. | |
| 4,808,169 A | 2/1989 | Haber et al. | |
| 4,813,426 A | 3/1989 | Haber et al. | |
| 4,813,936 A | 3/1989 | Schroeder | |
| 4,820,275 A | 4/1989 | Haber et al. | |
| 4,826,484 A | 5/1989 | Haber et al. | |
| 4,826,489 A | 5/1989 | Haber et al. | |
| 4,838,863 A | 6/1989 | Allard et al. | |
| 4,838,869 A | 6/1989 | Allard | |
| 4,841,985 A | 6/1989 | Wanamaker | |
| 4,850,968 A | 7/1989 | Romano | |
| 4,850,977 A | 7/1989 | Bayless | |
| 4,861,338 A | 8/1989 | Mathiesen et al. | |
| 4,874,382 A | 10/1989 | Lindemann et al. | |
| 4,900,307 A | 2/1990 | Kulli | |
| 4,904,242 A | 2/1990 | Kulli | |
| 4,908,022 A | 3/1990 | Haber | |
| 4,915,692 A | 4/1990 | Verlier | |
| 4,919,657 A | 4/1990 | Haber et al. | |
| 4,921,486 A | 5/1990 | DeChellis et al. | |
| 4,927,414 A | 5/1990 | Kulli | |
| 4,932,944 A * | 6/1990 | Jagger et al. | 604/192 |
| 4,935,015 A | 6/1990 | Hall | |
| 4,946,446 A | 8/1990 | Vadher | |
| 4,947,863 A | 8/1990 | Haber et al. | |
| 4,950,241 A | 8/1990 | Ranford | |
| 4,950,251 A | 8/1990 | Haining | |
| 4,955,870 A | 9/1990 | Ridderheim et al. | |
| 4,966,593 A | 10/1990 | Lennox | |
| 4,973,316 A | 11/1990 | Dysarz | |
| 4,978,340 A | 12/1990 | Terrill et al. | |
| 4,978,343 A | 12/1990 | Dysarz et al. | |
| 4,988,339 A | 1/1991 | Vadher | |
| 4,994,034 A | 2/1991 | Botich et al. | |
| 4,997,423 A | 3/1991 | Okuda et al. | |
| 4,998,921 A * | 3/1991 | Vickroy et al. | 604/167.02 |
| 5,000,736 A | 3/1991 | Kaufhold, Jr. et al. | |
| 5,000,738 A | 3/1991 | Lavallo et al. | |
| 5,007,903 A | 4/1991 | Ellard | |
| 5,019,044 A | 5/1991 | Tsao | |
| 5,026,354 A | 6/1991 | Kocses | |
| 5,030,208 A | 7/1991 | Novacek et al. | |
| 5,046,508 A | 9/1991 | Weissler | |
| 5,049,133 A | 9/1991 | Villen Pascual | |
| 5,053,010 A | 10/1991 | McGary et al. | |
| 5,061,249 A | 10/1991 | Campbell | |
| 5,064,419 A | 11/1991 | Gaarde | |
| 5,066,281 A | 11/1991 | Stevenson-Michener | |
| 5,067,942 A | 11/1991 | Jaffe et al. | |
| 5,067,948 A * | 11/1991 | Haber et al. | 604/192 |
| 5,084,018 A | 1/1992 | Tsao | |
| 5,088,986 A | 2/1992 | Nusbaum | |
| 5,092,853 A | 3/1992 | Couvertier. II | |
| 5,098,402 A | 3/1992 | Davis | |
| 5,112,315 A | 5/1992 | Gloyer et al. | |
| 5,112,318 A | 5/1992 | Novacek et al. | |
| 5,114,404 A | 5/1992 | Paxton et al. | |
| 5,114,410 A | 5/1992 | Caralt Batlle | |
| 5,116,326 A * | 5/1992 | Schmidt | 604/263 |
| 5,120,310 A | 6/1992 | Shaw | |
| 5,122,123 A * | 6/1992 | Vaillancourt | 604/192 |
| 5,122,124 A | 6/1992 | Novacek et al. | |
| 5,125,898 A | 6/1992 | Kaufhold, Jr. et al. | |
| 5,147,309 A * | 9/1992 | Hemmerich et al. | 604/192 |
| 5,151,089 A | 9/1992 | Kirk, III et al. | |
| 5,152,750 A | 10/1992 | Haining | |
| 5,163,907 A | 11/1992 | Szukiewicz | |
| 5,180,369 A | 1/1993 | Dysarz | |
| 5,180,370 A | 1/1993 | Gillespie | |
| 5,188,599 A | 2/1993 | Botich et al. | |
| 5,188,613 A | 2/1993 | Shaw | |
| 5,190,526 A | 3/1993 | Murray et al. | |
| 5,201,710 A | 4/1993 | Caselli | |
| 5,205,823 A | 4/1993 | Zdeb | |
| 5,205,824 A | 4/1993 | Mazur | |
| 5,205,827 A | 4/1993 | Novacek et al. | |
| 5,211,628 A | 5/1993 | Marshall | |
| 5,211,629 A | 5/1993 | Pressly et al. | |
| 5,211,630 A | 5/1993 | Schmahmann | |
| 5,219,338 A | 6/1993 | Haworth | |
| 5,221,262 A | 6/1993 | Kite | |
| 5,222,944 A | 6/1993 | Harris | |
| 5,226,893 A | 7/1993 | Kayser | |
| 5,232,458 A | 8/1993 | Chen | |
| 5,242,400 A | 9/1993 | Blake, III et al.. | |
| 5,242,402 A | 9/1993 | Chen | |
| 5,242,405 A | 9/1993 | Howe | |
| 5,250,031 A | 10/1993 | Kaplan et al. | |
| 5,267,961 A | 12/1993 | Shaw | |
| 5,273,544 A * | 12/1993 | Van Der Wal | 604/192 |
| 5,300,030 A | 4/1994 | Crossman et al. | |
| 5,324,265 A | 6/1994 | Murray et al. | |
| 5,342,308 A | 8/1994 | Boschetti | |
| 5,342,310 A | 8/1994 | Ueyama et al. | |
| 5,364,387 A | 11/1994 | Sweeney | 604/411 |
| 5,376,075 A | 12/1994 | Haughton et al. | |
| 5,385,551 A | 1/1995 | Shaw | |
| 5,389,076 A | 2/1995 | Shaw | |
| 5,407,431 A | 4/1995 | Botich et al. | |
| 5,407,436 A | 4/1995 | Toft et al. | |
| 5,423,758 A | 6/1995 | Shaw | |
| 5,578,001 A | 11/1996 | Shah | |
| 5,578,011 A | 11/1996 | Shaw | |
| 5,584,819 A | 12/1996 | Kopfer | 604/239 |
| 5,613,952 A | 3/1997 | Pressly, Sr. et al. | |
| 5,685,863 A * | 11/1997 | Botich et al. | 604/263 |
| 5,782,804 A | 7/1998 | McMahon | |
| 5,800,403 A | 9/1998 | Pressly, Sr. et al. | |
| 5,928,205 A * | 7/1999 | Marshall | 604/263 |
| 6,074,379 A | 6/2000 | Pressly, Sr. et al. | |
| 6,077,247 A * | 6/2000 | Marshall et al. | 604/192 |

FOREIGN PATENT DOCUMENTS

| | | | |
|---|---|---|---|
| EP | 0 427 861 A1 | 5/1991 | A61M/5/32 |
| EP | 0438368 A1 | 7/1991 | |
| EP | 0515766 A1 | 12/1992 | |
| EP | 0609167 A1 | 8/1994 | |
| EP | 0 820 778 A1 | 1/1998 | A61M/5/31 |
| EP | 0820779 A | 1/1998 | |
| FR | 2652006 | 6/1986 | |
| GB | 847913 | 9/1960 | |
| GB | 1284154 | 8/1972 | |
| GB | 1593512 | 7/1981 | |
| GB | 2197792 A | 6/1988 | |
| GB | 2242631 A | 3/1994 | |
| HU | 206457 | 11/1992 | |

| | | | | | | |
|---|---|---|---|---|---|---|
| JP | 02146773 | 6/1990 | | WO | WO 90/03196 | 4/1990 |
| NL | 8900208 | 1/1989 | | WO | WO 90/06146 | 6/1990 |
| TW | 142558 | 4/1979 | | WO | WO 90/07948 | 7/1990 |
| TW | 154735 | 6/1979 | | WO | WO 91/04066 | 4/1991 |
| TW | 167913 | 3/1980 | | WO | WO 92/21396 | 5/1992 |
| TW | 216518 | 6/1980 | | WO | WO 92/18187 | 10/1992 |
| TW | 225161 | 5/1982 | | WO | WO 93/12830 | 7/1993 |
| TW | 154735 | 3/1991 | | WO | WO 94/04207 | 3/1994 |
| TW | 216518 | 11/1993 | | WO | WO 00/13727 A | 3/2000 |
| TW | 225161 | 6/1994 | | | | |
| WO | WO81/03280 A | 11/1981 | | | | |
| WO | WO 89/00435 | 1/1989 | | | | |

\* cited by examiner

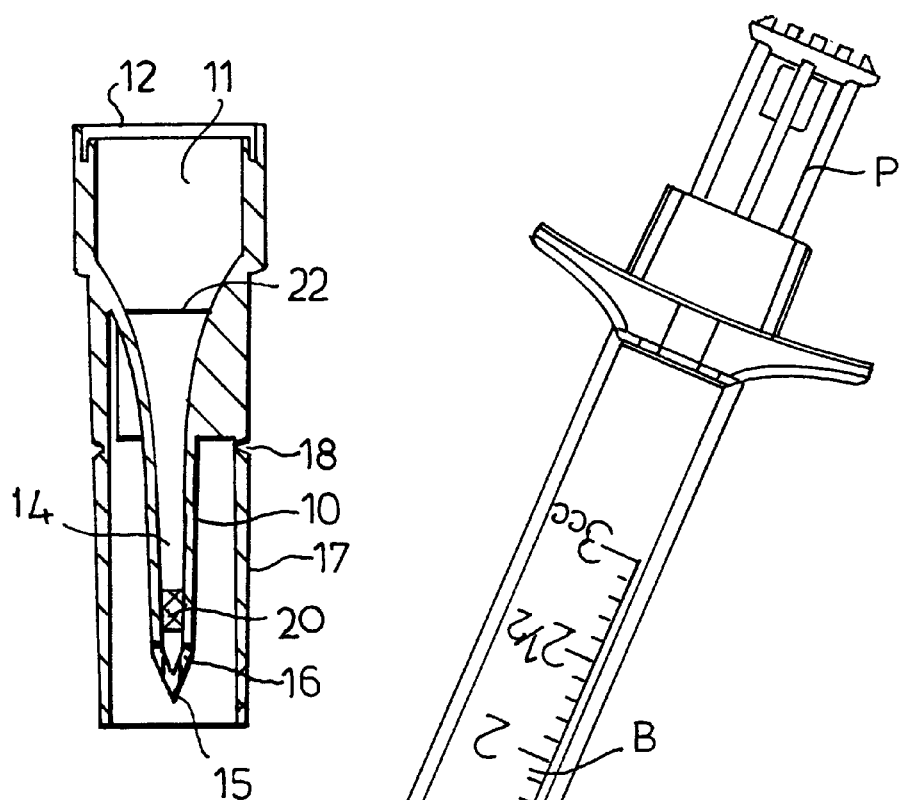
FIG.1
FIG.2
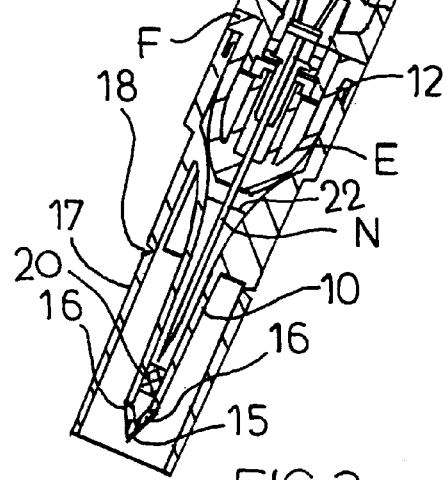
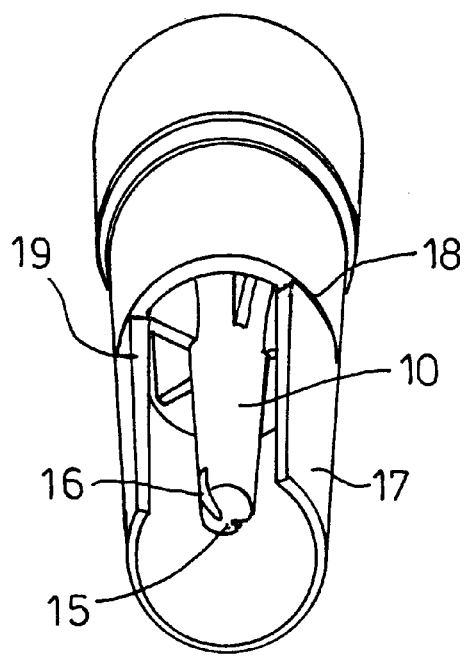
FIG.3

NEEDLE SHEATH

This application is a continuation of PCT/GB99/01175, filed Jul. 7, 1999.

This invention concerns a sheath for the needle of a hypodermic syringe.

Hypodermic syringe assemblies are usually provided with a protective sheath covering the needle for its protection until the syringe is required for use.

It is a common, though by no means universal, practice to change the needle of a syringe after filling and before administration of the injection because of a perception that the original needle may become blunted, bent or subjected to loss of needle lubricant during the filling operation, for example by insertion through the rubber cap of the vial, contaminated with a foreign substance, for example latex from such a cap or rendered unsterile.

In the case of syringes with provision for retraction of the needle after use as disclosed for instance in our prior EP-A-0776225, the needle assembly tends to be specially designed for this purpose and it is not therefore practical to contemplate changing needles after filling the syringe and before administering the injection.

There are also concerns over the risks of drawing in fragments or slivers of material, e.g. glass, when the syringe is filled from for example an ampoule following breaking of a glass or other cap of the ampoule. Moreover, if the same needle is used to fill the syringe and also administer the medication, some injection fluid may be present on the outside of the needle which may be undesirable since some substances for injection can be irritating to the skin.

These matters are addressed by various aspects of the present invention. The invention has particular, but not necessarily exclusive, application to the type of syringe which incorporates a needle retraction mechanism and is thereby not readily amenable to the possibility of needle change between syringe filling and admistration of the injection.

According to one aspect of the present invention there is provided a hypodermic syringe having a barrel, a hollow fluid dispensing needle which projects from the barrel, means for retracting the needle after use from the projecting position to a retracted, inaccessible position, and a sheath which is removably engageable with the syringe to sheath the needle and provide an interior zone for communication with the internal bore of the needle, the sheath being apertured to admit liquid to said zone whereby liquid drawn through the needle into the syringe first passes into said zone.

The sheath may be shaped or adapted so as to be capable of penetrating the rubber cap of a vial or the like. To this end, it may be provided with a pointed end or a separate needle. In this way, the sheath may be used as a needle during filling of the syringe thereby avoiding any risk of compromising the needle proper as discussed above through having to use the needle proper to pierce a rubber cap for instance.

When used with a syringe having needle retraction means, the needle need only be exposed during the time that it is actually in use for the administration of an injection. At all other times, including filling of the syringe, the needle may be effectively inaccessible thereby considerably reducing the risk of needle stick injuries since the sheath need not be particularly sharp as it is only used for filling the syringe.

It will be appreciated that the sheath is not limited to use with syringes of the type provided with needle-retracting means.

According to a second aspect of the present invention there is provided a sheath which sealably connects over the needle of a hypodermic syringe and is optionally shaped or adapted to penetrate the rubber cap of a vial or the like, the sheath being apertured to allow the ingress of liquid to an interior zone thereof whereby liquid drawn through the needle into the syringe first passes into said zone, filter means being incorporated in the sheath to exclude the entry of particulate material into said zone.

According to a further aspect of the present invention there is provided a sheath which sealably connects over the needle of a hypodermic syringe and is optionally shaped or adapted to penetrate the rubber cap of a vial or the like, the sheath being apertured to allow the ingress of liquid to an interior zone thereof whereby liquid drawn through the needle into the syringe first passes into said zone, needle-wiping means being incorporated in the sheath and arranged so that removal of the sheath automatically wipes the needle to remove any excess liquid on the outside thereof.

The sheath may, if desired, incorporate both filter means and needle-wiping means.

The filter means may be be take take various forms—for example the filter means may be composed of fibrous material or it may comprise a sintered plastics material. Examples of suitable materials include hydrophilic and hydrophobic materials. The plastics materials employed may for instance be selected from the following, including combinations thereof: nylon, polyurethane, polyester, polyolefin, polyethylene, PTFE, acetal, acrylonitrile butadiene styrene and styrene acrylonitrile. Most of these materials can be processed in a number of ways with the exception of PTFE which will generally be sintered. The other materials can be moulded with a foaming agent to give an open cell foam with controllable porosity or made into a non-woven fibrous mat by using a binder compound. Suitable filter materials for use in the present invention are obtainable from for example GVS Srl of Bologna, Italy and Filtertek BV of Limerick, Eire.

The needle-wiping means is conveniently in the form of a thin web or membrane through which the needle extends in use so that when the sheath is removed from the sheath, the marginal edge of the web or membrane surrounding the needle is drawn along the outside the needle thereby wiping the same. Preferably the web or membrane is composed of a resilient material and tends to contract around the needle by virtue of its resilient nature. Suitable materials for the membrane or web include elastomers such as silicones or silicone-based materials.

The sheath may have a pointed end to facilitate penetration into a vessel, e.g. via a rubber seal or cap provided on the vessel.

The sheath may have at least one aperture through its wall above the pointed end and/or it may have an aperture at its pointed end.

The sheath may be protected before use by a removable guard which is conveniently in the form of a part cylindrical wall.

The guard may be integral with the sheath and removable at one or more frangible connections.

The sheath may be removably attachable to the syringe through a push-on/pull-off friction fit or snap fit or through a threaded connection or a bayonet-type connection.

The sheath may be formed from a metal or a plastics material.

The invention will be further apparent from the following description with reference to the several figures of the accompanying drawing which show, by way of example only, several forms of sheath embodying same. In the drawings:

FIG. 1 shows a cross-section through the sheath;

FIG. 2 shows a cross-section through the sheath of FIG. 1 in position over the needle of a hypodermic syringe;

FIG. 3 shows a perspective view of the sheath of FIGS. 1 and 2;

Figure 4:
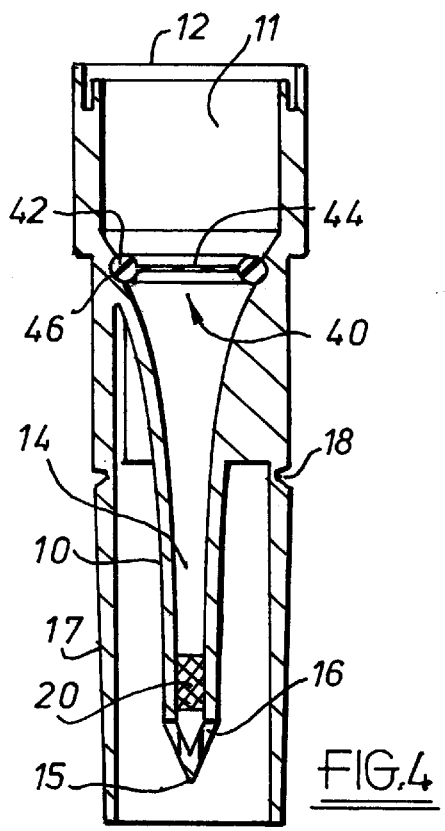
FIG. 4 is a fragmentary sectional view showing one specific form that the wiping membrane may take.

Referring now to FIGS. 1 to 3 of the drawings, the sheath 10 is formed, e.g. from metal or a plastics material, with a socket 11 at its rear end for engagement with the end cap E of a hypodermic syringe having a needle N, barrel B and plunger P. The sheath may engage with the syringe with push-on/pull-off friction fit. An annular seal 12 is provided on the end of the sheath 10 which abuts the forward face of an annular flange F at the rearward end of the cap E.

The sheath 10 has a hollow interior 14 which accommodates the needle N of the syringe. The sheath 10 terminates in a pointed forward end 15 capable of penetrating the rubber cap of a vial or being inserted into an ampoule whose cap has been broken therefrom. The sheath is apertured at a location in close proximity to the pointed end 15, the aperture being formed by an axially extending elongate slot. In the illustrated embodiment, two such slotted apertures 16 are provided on diametrically opposite sides of the sheath.

A guard 17 in the form of a part cylindrical wall is formed integrally with the sheath 10 and is removable from the sheath at a frangible connection 18. The guard protects the sheath and prevents its pointed end from damaging and thereby compromising the sterility of primary packaging in which the syringe is supplied. The slot 19 in the wall enables the guard to be broken away without damaging the sheath which can pass through the slot 19 during this operation.

A filtering material depicted by reference numeral 20 is provided within the sheath at a location between the forward end of the needle and the apertures 16 so that only liquid that has passed through the filtering material is accessible by the needle during filling. In this way, particulate materials, such as glass slivers, splinters or shards that may have inadvertantly contaminated the injection fluid are excluded by the filtering material thereby eliminating any risk of fine slivers of glass entering the syringe during filling thereof. The filter material may take various forms, e.g. it may be in the form of a fibrous extrusion or a porous plastic plug.

At a suitable location, the sheath is provided with needle-wiping means which, in the illustrated embodiment, is in the form of a thin web of material or membrane 22, e.g. an elastomer such as a suitable silicone, extending across the interior of the sheath so that, when the latter is assembled to the syringe, the needle passes through the web. The web may be provided with a pre-formed hole through which the needle passes or the hole may be formed by the needle automatically during the act of pushing the sheath on to the syringe. In either case, the arrangement is such that the marginal edge around the hole in the web contacts the needle around its circumference so that, when the sheath is subsequently removed, the marginal edge cleans off any excess liquid adhering to the outside of the needle following the filling operation. The membrane 22 may be of an elastomeric material such as silicone rubber.

In use, the syringe is removed from its primary packaging and the barrel B of the syringe filled in known manner by retraction of the plunger P after insertion of the forward end of the sheath through the rubber cap of a vial or insertion of the forward end into an ampoule whose cap has been broken therefrom. During filling, the injection liquid passes through the filtering material before entry into the needle. The sheath 10 is then removed and discarded to enable administration of the injection in known manner. During sheath removal, the outside of the needle is automatically wiped clean.

It sometimes happens that medical staff use a filling needle of larger bore than the injection needle for the purposes of filling the syringe—particularly when the bore of the injection needle is particularly fine. The possibility of removing the sheath 10 and original needle before replacing the sheath 10 and using it as a filling needle should not be overlooked.

Referring now to FIG. 4, the needle-wiping means 40 may in one embodiment of the invention be in the form of a disc comprising a peripheral ring 42, e.g. of O-section, and an integral central web 44. The disc is assembled to the sheath by seating the O-ring firmly, preferably with a sealing engagement, in an annular groove 46 formed in the wall 48 of the sheath 10. Typically the disc comprises an elastomeric material. When the sheath is assembled to the syringe, the needle will penetrate the central web which, by virtue of its elastomeric nature, will seal around the outer periphery of the needle. The web may be initially imperforate or it may be preformed with an aperture through which the needle passes. In this way, when the tip of the sheath is inserted into a liquid to be drawn into the syringe, the interior volume within the sheath between the central web 44 and the tip of the sheath may be made airtight to allow suction to be developed.

Figure 5:
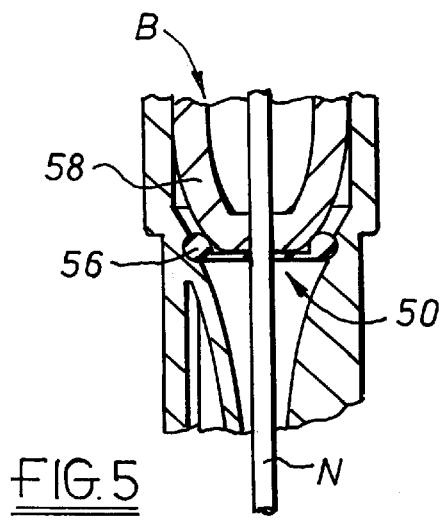
FIG. 5 is a fragmentary sectional view showing a needle-wiping membrane in the form of a disc which provides sealing engagement between the sheath and the nose of the syringe barrel.
Figure 5A:
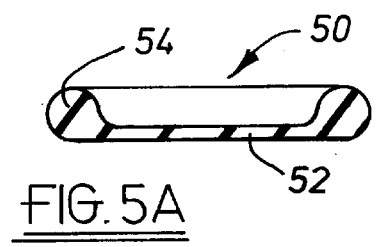
FIG. 5A is a sectional view showing the disc of FIG. 5.

FIGS. 5 and 5A illustrate another form of needle-wiping disc 50 designed to effect a seal with the nose 58 of the barrel B. The disc 50 comprises a web 52 from one face of which an upstanding generally O-section ring 54 projects. The ring 54 seats in a groove 56 of the sheath 10 so that, on assembly of the sheath to the barrel, the ring 54 is engaged between the sheath and barrel to form an air-tight seal. As in the previous embodiments, the disc is fabricated from an elastomeric material and the web is sufficiently thin that it is readily pierced by, and seals around, the needle during assembly of the sheath to the barrel. In this instance, sealing is effected by the disc 50 at two locations, namely around the needle itself and also at the point of contact with the nose 58 of the barrel B.

Figure 6:
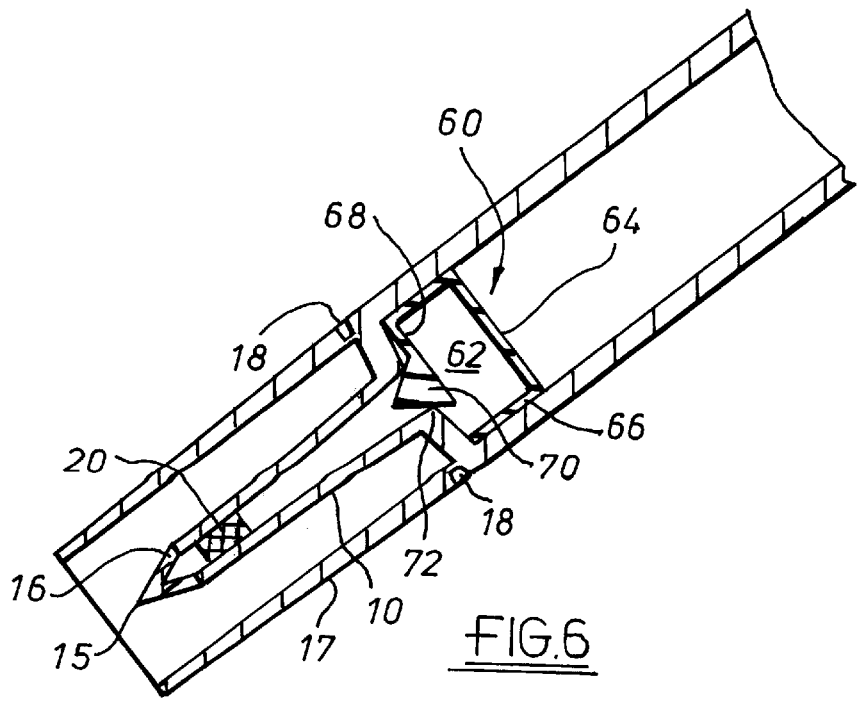
FIG. 6 is a fragmentary sectional view illustrating another form of needle-wiping membrane and a one-way valve arrangement.
Figure 6A:
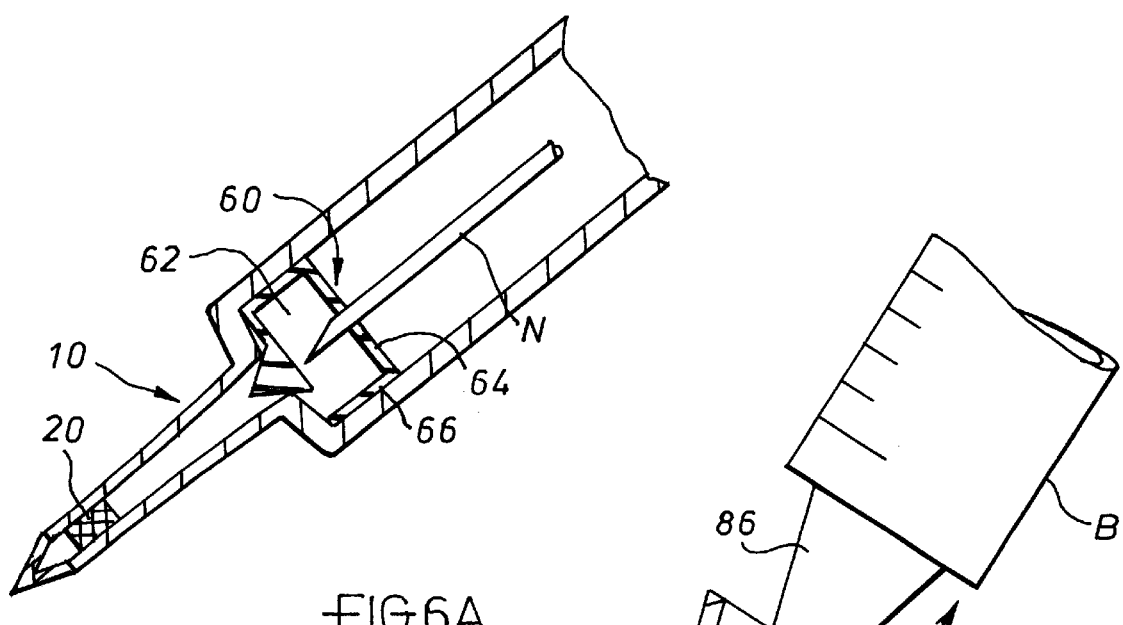
FIG. 6A is a similar view to that of FIG. 6 showing the membrane pierced by the needle of the syringe.

In the embodiment of FIGS. 6 and 6A, in addition to the seal between the sheath and the interior of the needle, there is also a one-way valve which ensures that the flow of fluid can only take place in one direction when the sheath is fitted to the syringe. In FIG. 6, those parts in common with FIGS. 1 to 3 are depicted by the same reference numerals and will not be described further. As shown in FIG. 6, a one-piece moulding 60 is located within the interior of the sheath and forms a one-way valved septum chamber 62 comprising a web 64 which extends across the cross-section of the sheath to form a seal which isolates the lower interior volume of the sheath extending between the web 64 and the tip 15 of the sheath from the upper interior volume extending between the web 64 and the nose of the barrel B. The moulding includes a generally cylindrical side wall 66 which nests within the interior of the sheath and a wall 68 which includes an enlargement 70 forming a valve member normally seats against and makes sealing engagement with the upper end of the passageway 72 extending through the projecting spike-like formation of the sheath 10. The wall 68 only extends only partway across the diameter of the moulding in such a way that it can flex towards the wall 64 by flow of liquid through the spike-like formation of sheath 10. In the absence of liquid ingress, the wall 68 biases the valve member 70 to its closed position in which it closes the upper end of the hollow spike-like formation.

In use, when the sheath has been assembled to the syringe, the needle N pierces the web 64 and penetrates into the septum chamber 62 (see FIG. 6A). When the cylindrical guard 17 has been removed and the tip of sheath is immersed in a liquid, the syringe is operated to aspirate the liquid through the needle N so that the resulting suction effect draws the valve member 70 away from its seating 72 at the upper end of the spike-like formation to draw the liquid upwardly into the septum chamber 62 and then into the needle to fill the syringe. Also, liquid drawn into the needle N in this way must first traverse the filter 20 and any glass shards or contaminants present may be excluded from passing into the septum chamber 62 and hence the syringe. Flow of liquid in the opposite direction is prevented since such flow will tend to cause the valve member 70 to make sealing contact with the seat 72 at the upper end of the spike-like formation and thereby block liquid flow.

Subsequently the sheath 10 may be removed from the syringe prior to using the syringe to administer an injection to the patient. In the course of removing the sheath the web 64, which by virtue of its resilient nature contracts around the needle, is drawn along the forward extremity of the needle thereby wiping any excess liquid from the exterior of the needle before it is used to inject a patient. It will be observed that the one-way valve ensures that the injection can only be administered after the sheath has been removed from the syringe thereby eliminating the possibility of an injection being administered while the sheath is still in place.

Figure 7:
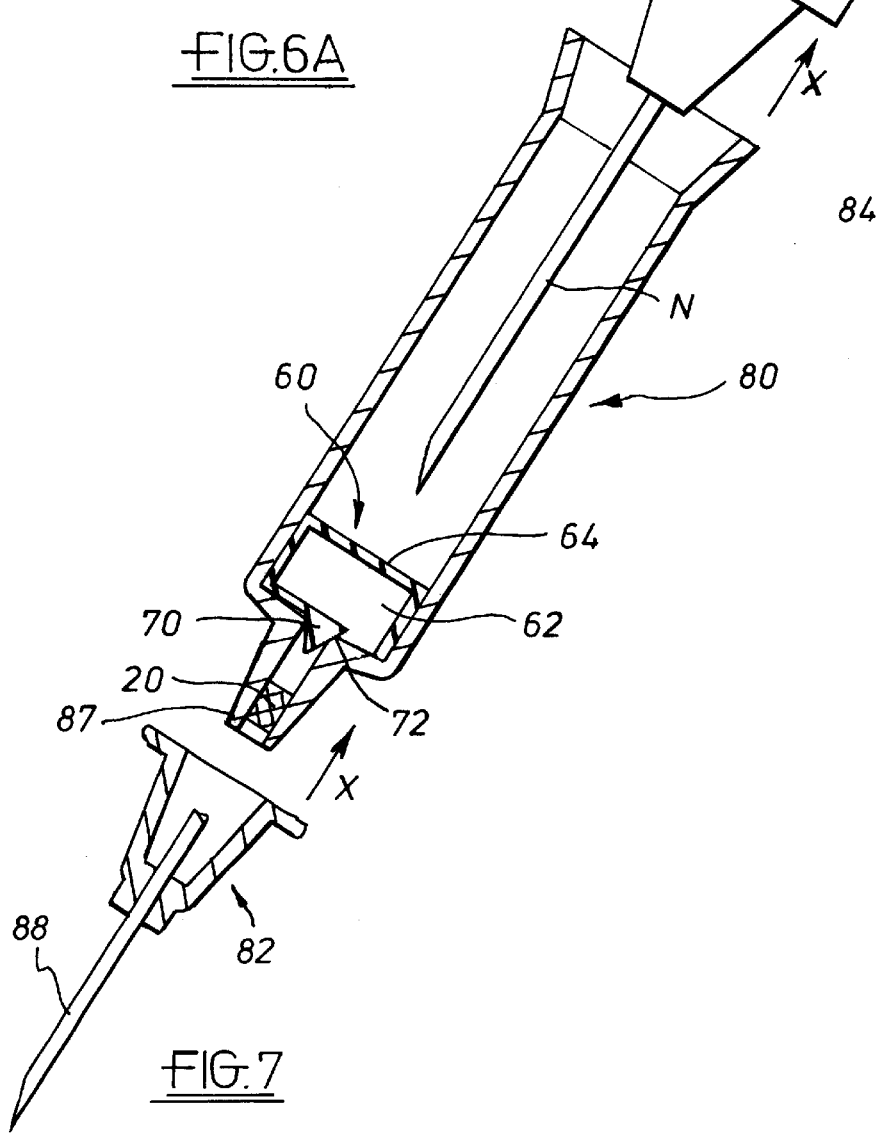
FIG. 7 is diagrammatic, exploded view of another embodiment of the sheath in which the sheath is of two-part construction including a separate filling needle.

In the embodiments thus far described, the sheath is generally spike-shaped so that it can be used to penetrate or pierce the rubber cap of a vial directly. FIG. 7 illustrates an embodiment in which the sheath is of two-part construction comprising an adaptor section 80 which may incorporate the wiper and/or the filter and a separate auxiliary needle-carrying section 82. The adaptor section 80 at its upper end 84 is adapted to be releasably engaged with the nose 86 of the syringe barrel B. For example, it may be a simple push fit (in the direction X) on to the barrel nose 86 and, when so fitted, it may form a fluid-tight seal although this is not essential if the wiping membrane serves this purpose. As in the embodiment of FIGS. 6 and 6A, the wiper membrane 64 is embodied in a one-piece moulding 60 of an elastomeric material which also incorporates a one-way valve 70 co-operating with seat 72, the arrangement being such that when the sheath is fitted to the barrel, the needle N pierces the membrane 64 and communicates with the septum volume 62 (in the manner shown in FIG. 6A). The membrane 64 serves the dual function of providing a seal around the needle N when the sheath is correctly assembled to the syringe and wiping the needle N on removal of the sheath from the syringe.

The forward end 87 of the adaptor section 80 and the needle-carrying section 82 are designed to fit together with a sealing engagement, e.g. by means of a luer slip or luer lock fitting. The forward end 87 accommodates a plug 20 of filter material so that liquid entering the septum chamber 62 must first traverse the filter thereby excluding foreign matter such as glass shards that might be present when the syringe is filled from a glass ampoule. The needle 88 of section 82 is employed purely as a filling needle which is used to pierce the rubber cap of a vial for example, liquid being drawn into the syringe via the needle 88, one-way valve 70, septum chamber 62 and needle N by appropriate operation of the syringe plunger. After the filling operation has been completed, the section 82 is removed and discarded while the adaptor section 80 can be left in place until the syringe is used to administer the injection.

In each of the embodiments described above, the syringe may be of the type provided with a needle retraction mechanism whereby, after administration of the injection, the needle N is retracted from the projecting position illustrated to an inaccessible position so as to prevent needle stick injuries. A suitable needle retraction mechanism for use in the present invention is that disclosed in EP-A-0776225, the entire disclosure of which is incorporated herein by this reference.

Figure 8:
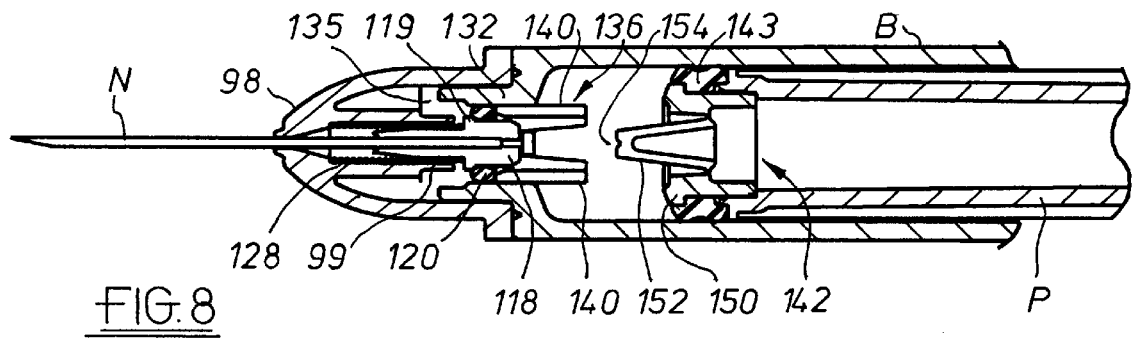
FIG. 8 is fragmentary sectional view of the syringe showing the same in at a stage in which the plunger has completed part of its forward travel.
Figure 9:
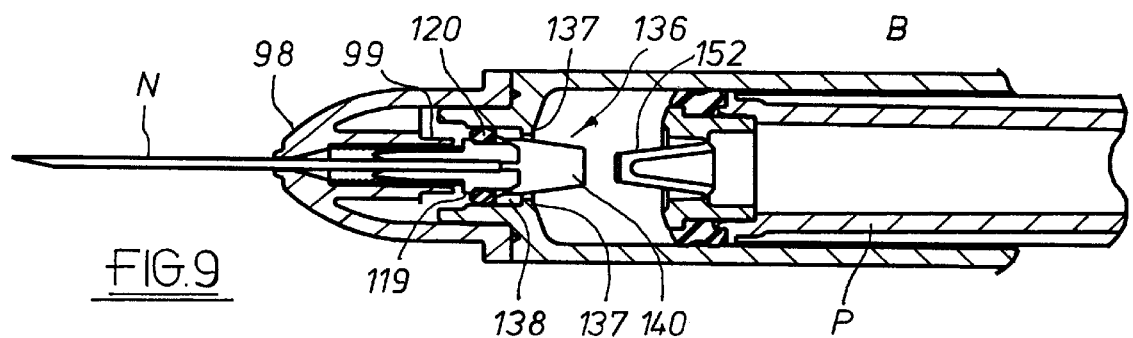
FIG. 9 is a view which is rotated 90 degrees relative to that of FIG. 8 and showing the syringe in the same condition as in FIG. 8.

One embodiment of the needle retraction mechanism will now be described with reference to FIGS. 8 to 15. The barrel B of the syringe includes a mounting portion 98 for the needle N, having a through passage at the inner end of which is an upstanding annular wall 99. The inner end of the needle N is axially captive with a hub 118 having an annular flange 119 which locates an O-ring 120. The hub 118 provides a passageway for the needle N. A compression spring 128 surrounds the needle so as to bias the hub 118 and hence the needle rearwardly. When assembled, the spring 128 is in an almost fully compressed condition and is maintained in that condition by the O-ring 120 which is compressed between annular wall portion 132 and the hub 118. The O-ring 120 is prevented from movement in the rearward direction by a crown 136 which is, itself, blocked from rearward movement by projections 137 (see FIG. 9). The crown 136 comprises a ring 138 provided with a pair of rearwardly directed extensions 140 of arcuate configuration, the dimension of the ring 138 and the spacing of the extensions being sufficient to allow the needle hub to pass during the needle retraction phase as described below. The extensions 140 project into the interior of the barrel when the syringe is in its pre-use condition shown in FIG. 8. As seen in FIG. 8, there is an annular space 135 forwardly of the O-ring 120.

The plunger P of the syringe is hollow having its rear end (not shown in FIGS. 8 to 15) closed by a cap. The forward end of the plunger P is provided with an insert 142 which engages firmly in the plunger and is encircled by seal 143 which contacts the internal surface of the barrel B. The insert 142 constitutes a "bursting disc" device and includes an annular rim portion 150 and a central generally frusto-conical formation 152 which is connected to the rim portion 150 in a frangible fashion, e.g. by a thin web of material which can be ruptured or broken away when the central formation 152 is stressed axially relative to the rim portion. In operation, the syringe is charged with liquid via the sheath 10 as described previously to achieve its ready-for-use condition in which the plunger P is drawn back rearwardly relative to the barrel B. After removal of the sheath 10 (not shown in FIGS. 8 to 15), the plunger P is caused to move forwardly relative to the barrel (i.e. to the left as seen in FIGS. 8 to 15) and the advancing plunger is effective to expel liquid through the needle N.

Figure 10:
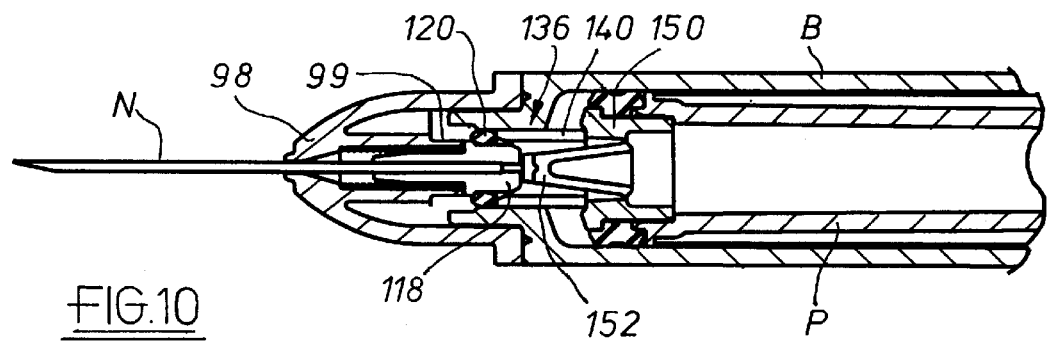
FIGS. 10 to 15 are views similar to that of FIG. 8 but showing successive stages of plunger forward travel up to and including completion of drug dispensing and operation of the needle retraction mechanism.
Figure 11:
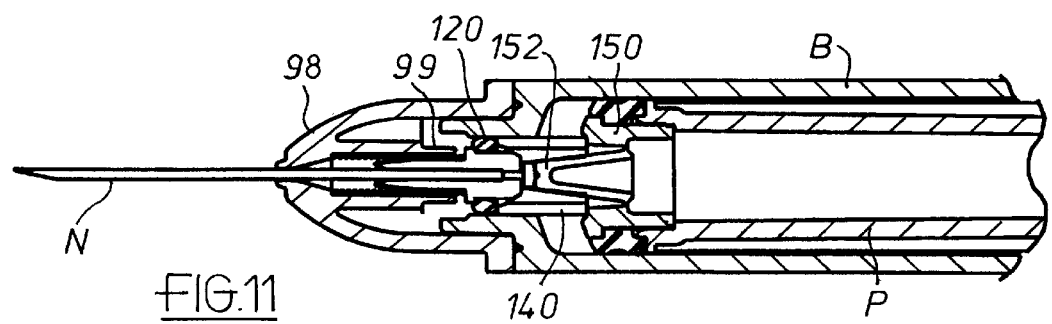
Figure 12:
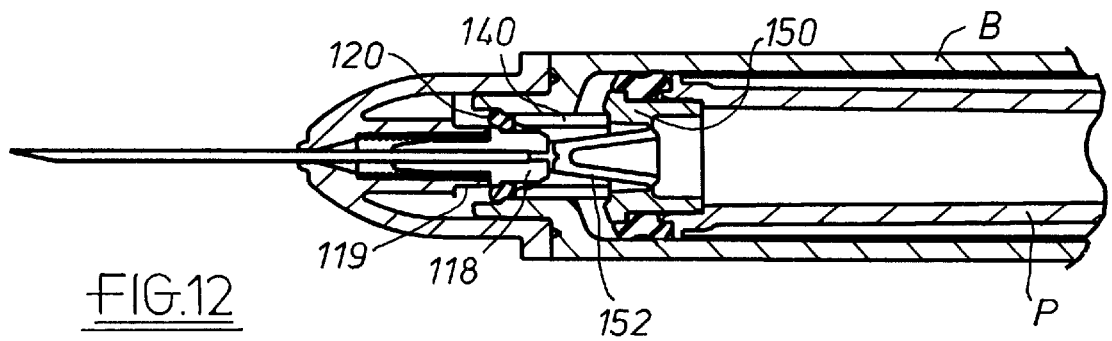

FIG. 10 shows the positions of the parts after the plunger P has been advanced sufficiently to bring the leading end face of the rim portion 150 into abutment with the trailing ends of the extensions 140. Further forward travel of the plunger P is effective to push the crown 136 forwardly (by virtue of contact between the rim portion 150 and the extensions 140), which forward movement is transmitted to the needle hub 118 through the O-ring 120 thereby taking up the small amount of axial play initially present between the flange 119 and the trailing end of the annular wall 99 and terminating any further forward movement of the needle hub. With hub 119 blocked by wall 99, continued forward movement of the plunger P is then effective to begin displacing the O-ring 120 as shown in FIG. 12, i.e. the O-ring then begins to expand over the flange 119 of the hub.

Figure 13:
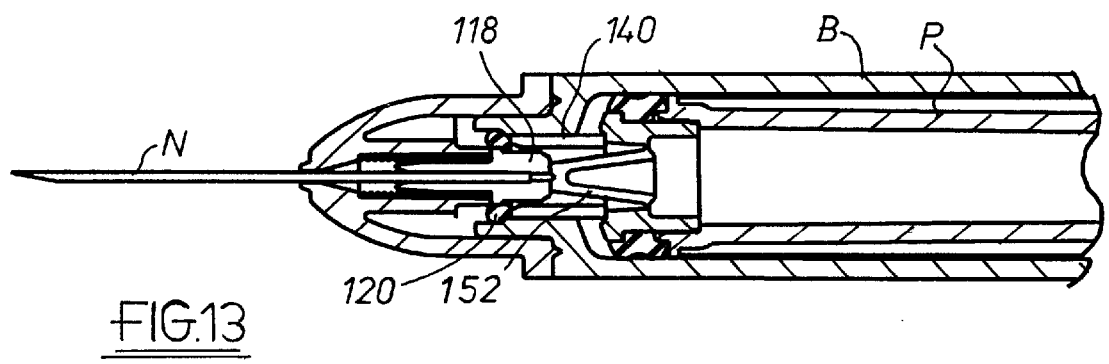
Figure 14:
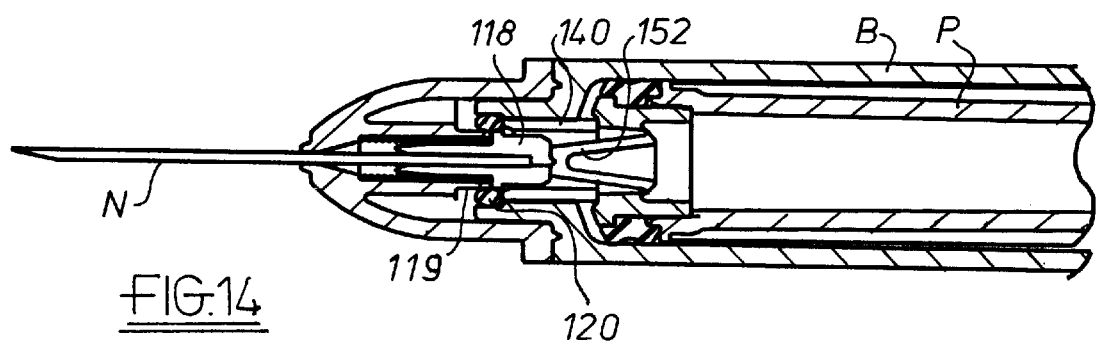
Figure 15:
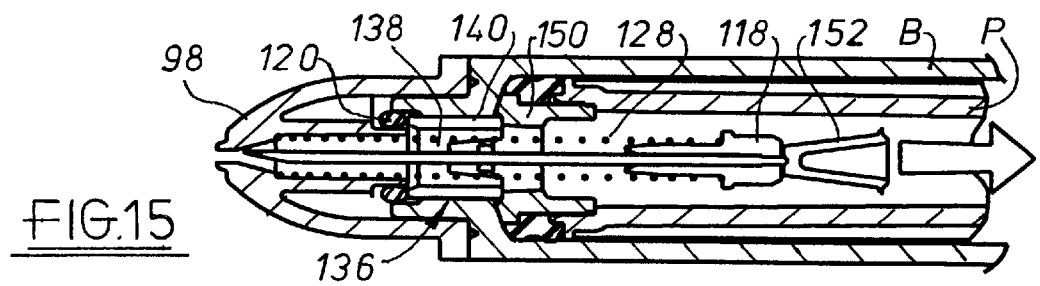

As shown in FIG. 13, the foward end of the formation 152 eventually comes into contact with the rear face of the needle hub 118. At this stage, the O-ring 120 is still effective to maintain a seal and drug continues to be expelled from the barrel via a slot 154 in the forward end face of the formation 152. Once the formation 152 has come into contact with the needle hub 118, continued pressure applied to the plunger in the forward direction is effective to stress the thin web interconnecting the formation 152 and the rim portion 150 and deform the web towards its breaking point. Before the web breaks however, the arrangement is such that web integrity is maintained until such time as O-ring 120 has been fully pushed over the flange 119 and onto the annular wall 99 (see FIG. 14) so as to disable the coupling action afforded by the O-ring between the needle hub and the crown. The procedure is completed by breakage of the thin web thus allowing the spring 128 to expand and drive the needle hub and connected needle N rearwardly together with the broken away formation 152 into the interior of the plunger thereby rendering the needle inaccessibly concealed wholly within the syringe as shown in FIG. 15.

It will be seen that the needle N need only be exposed during the administration of the intended injection. At all other times, the needle may be either sheathed with the aid of sheath or inaccessible as a result of being retracted into the plunger (and hence the barrel).

It will be appreciated that it is not intended to limit the invention to the examples given herein; many varaiations, such as might readiliy occur to one skilled in the art, being possible, without departing from the scope thereof. Thus, for example, the pointed end of the sheath as shown in Figures may have a single forwardly facing aperture instead of the radial apertures described above. Again, for example, the guard may comprise a complete cylindrical wall, though more care is then required in its removal.

What is claimed is:

1. A hypodermic syringe having a barrel, a hollow fluid dispensing needle which projects from the barrel, a needle retractor operable to retract the needle after use from the projecting position to an inaccessible and inoperative position, and a sheath which is removably engageable with the syringe to sheath the needle and provide an interior zone for communication with the internal bore of the needle, the sheath being apertured to admit liquid to said zone whereby liquid drawn through the needle into the syringe first passes into said zone.

2. A syringe as claimed in claim 1 in which the sheath includes at least one filter element to exclude the entry of particulate material into said zone.

3. The syringe as claimed in claim 1 in which the inaccessible and inoperative position is within the body of the syringe.

4. A syringe as claimed in claim 1 including a plunger movable within the barrel to effect expulsion of liquid from the barrel and in which the needle retractor is automatically operable in response to travel of the plunger to a predetermined position within the barrel.

5. A syringe as claimed in claim 4 in which the needle has a needle retraction direction and said restraining structure includes a resilient O-ring carried by the needle, an axially movable member encircling the needle and engaging the O-ring, whereby the biasing member biases the axially movable member into abutment with a stop surface to prevent movement of the needle and the axially movable member in the needle retraction direction, the axially movable member being movable in the opposite direction by the plunger of the syringe to disengage the O-ring from the needle during the final part of plunger travel when dispensing and thereby free the needle for movement in the needle retraction direction.

6. A syringe as claimed in claim 1 wherein the needle inaccessible and inoperative position is a retracted position, said syringe including a biasing member biasing the needle to its retracted position and a needle restraining structure whereby movement of the needle to the retracted position is restrained.

7. A sheath which sealably connects over the needle of a hypodermic syringe and is adapted for penetrating the rubber cap of a vial or the like, the sheath being apertured to allow the ingress of liquid to an interior zone thereof whereby liquid drawn through the needle into the syringe first passes into said zone, at least one filter element being incorporated in the sheath to exclude the entry of particulate material into said zone.

8. A sheath as claimed in claim 7 in which said at least one filter element comprises a fibrous material.

9. A sheath as claimed in claim 7 in which said at least one filter element comprises a pug of porous plastics material.

10. A sheath as claimed in claim 7 in which the sheath includes at least one needle-wiping element so arranged that on removal of the sheath the needle is automatically wiped to remove any excess liquid on the outside thereof.

11. A sheath as claimed in claim 7 in which the sheath includes a one-way valve operable to allow fluid flow into said zone.

12. A sheath as claimed in claim 7 in which the sheath is of two-part construction comprising an adaptor section for assembly to the syringe and an auxiliary needle-carrying section releasably connected to the adaptor section, the filter element being located in the adaptor section.

13. In combination, the sheath as claimed in claim 7 and a syringe, the sheath being attachable to the syringe in such a way that the forward end of the needle extends into said zone.

14. A sheath which sealably connects over the needle of a hypodermic syringe and is adapted for penetrating the rubber cap of a vial or the like, the sheath being apertured to allow the ingress of liquid to an interior zone thereof whereby liquid drawn through the needle into the syringe first passes into said zone, at least one needle-wiping element being incorporated in the sheath and arranged so that removal of the sheath automatically wipes the needle to remove any excess liquid on the outside thereof.

15. A sheath as claimed in claim 14 in which said at least one needle-wiping element comprises a web or membrane extending across the path of insertion of the needle into the sheath during assembly of the latter to the syringe.

16. A sheath as claimed in claim 14 in which said at least one needle-wiping element also serves to provide a seal between said zone and the portion of the sheath which engages with the syringe.

17. A sheath as claimed in claim 14 in which said at least one needle-wiping element includes a portion for making sealing engagement with the syringe body.

18. A sheath as claimed in claim 14 in which said at least one needle-wiping element comprises a thin web or membrane through which the needle extends when the sheath is assembled to the syringe.

19. A sheath as claimed in claim 18 in which the web is pre-formed with a hole through which the needle extends.

20. A sheath as claimed in claim 18 in which the web is imperforate but made of a material which allows penetration of the needle to form its own hole in the course of assembling the sheath to the syringe.

21. A sheath as claimed in claim 18 in which the web or membrane is composed of a resilient material and tends to contract around the needle by virtue of its resilient nature thereby maintaining a sealing contact with the needle.

22. A sheath as claimed in claim 18 in which said at least one needle-wiping element comprises an elastomeric material.

23. A sheath as claimed in claim 14 in which the sheath is provided with a pointed end.

24. A sheath as claimed in claim 23 which the sheath has an aperture at the tip of its pointed end.

25. A sheath as claimed in claim 14 which the sheath is of two-part construction comprising an adaptor section for assembly to the syringe and an auxiliary needle-carrying section releasably connected to the adaptor section.

26. A sheath as claimed in claim 25 in which said zone is located within the adaptor section.

27. A sheath as claimed in claim 25, the needle-wiping element being located in the adaptor section.

28. A sheath according to claim 14 in which the sheath is attachable to the syringe by one of a push-on/pull-off friction fit, a threaded connection, and a bayonet connection.

29. A sheath as claimed in claim 14, in which the sheath terminates in an integral pointed tip.

30. A sheath as claimed in claim 29 in which the sheath has at least one aperture for ingress of liquid, the aperture being in the form of an elongated slot which terminates in close proximity to the forward extremity of said tip.

31. A sheath according to claim 14 which includes a removable guard.

32. A sheath according to claim 31 wherein the guard is in the form of a part cylindrical wall.

33. A sheath according to claim 31 wherein the guard is integral with the sheath and includes a frangible connection for separating the guard from the sheath.

34. A sheath according to claim 14 formed from a metal or a plastics material.

35. In combination, the sheath as claimed in claim 14 and a syringe, the sheath being attachable to the syringe in such a way that the forward end of the needle extends into said zone.

36. A sheath which sealably connects over the needle of a hypodermic syringe and is adapted for penetrating the rubber cap of a vial or the like, the sheath being apertured to allow the ingress of liquid to an interior zone thereof whereby liquid drawn through the needle into the syringe first passes into said zone, the sheath including a one-way valve operable to allow fluid flow into said zone.

37. A sheath as claimed in claim 36 which includes a filter element, the one-way valve being located between said zone and the filter element.

38. A sheath as claimed in claim 36 which includes a needle-wiping element, the needle-wiping element and the one-way valve being integral with each other.

* * * * *